(12) United States Patent
Abele et al.

(10) Patent No.: US 9,127,002 B2
(45) Date of Patent: Sep. 8, 2015

(54) PROCESS FOR MANUFACTURING A NAPHTHYRIDINE DERIVATIVE

(71) Applicant: Actelion Pharmaceuticals Ltd., Allschwil (CH)

(72) Inventors: Stefan Abele, Allschwil (CH); Gunther Schmidt, Allschwil (CH)

(73) Assignee: Actelion Pharmaceuticals Ltd, Allschwil (CH)

( * ) Notice: Subject to any disclaimer, the term of this patent is extended or adjusted under 35 U.S.C. 154(b) by 0 days.

(21) Appl. No.: 14/377,890

(22) PCT Filed: Feb. 8, 2013

(86) PCT No.: PCT/IB2013/051044
§ 371 (c)(1),
(2) Date: Aug. 11, 2014

(87) PCT Pub. No.: WO2013/118086
PCT Pub. Date: Aug. 15, 2013

(65) Prior Publication Data
US 2015/0025244 A1    Jan. 22, 2015

(30) Foreign Application Priority Data

Feb. 10, 2012  (WO) .................. PCT/IB2012/050609

(51) Int. Cl.
*C07D 471/04* (2006.01)

(52) U.S. Cl.
CPC ................... *C07D 471/04* (2013.01)

(58) Field of Classification Search
CPC .................................... C07D 471/04
USPC ...................................... 546/122
See application file for complete search history.

(56) References Cited

U.S. PATENT DOCUMENTS

| | | | |
|---|---|---|---|
| 8,211,890 | B2 | 7/2012 | Hubschwerlen et al. |
| 8,318,940 | B2* | 11/2012 | Alemparte-Gallardo et al. ............. 546/113 |
| 2004/0001970 | A1 | 1/2004 | Qiu et al. |
| 2011/0319424 | A1* | 12/2011 | Alemparte-Gallardo ........... 514/255.05 |
| 2014/0243302 | A1* | 8/2014 | Fukuda et al. ............. 514/192 |

FOREIGN PATENT DOCUMENTS

| | | |
|---|---|---|
| WO | 91/07404 | 5/1991 |
| WO | 02/08224 | 1/2002 |
| WO | 02/24684 | 3/2002 |
| WO | 02/50040 | 6/2002 |
| WO | 02/50061 | 6/2002 |
| WO | 02/056882 | 7/2002 |
| WO | 02/096907 | 12/2002 |
| WO | 03/010138 | 2/2003 |
| WO | 03/087098 | 10/2003 |
| WO | 2004/014361 | 2/2004 |
| WO | 2004/058144 | 7/2004 |
| WO | 2004/087647 | 10/2004 |
| WO | 2005/097781 | 10/2005 |
| WO | 2008/009700 | 1/2008 |
| WO | 2009/090222 | 7/2009 |
| WO | 2010/084152 | 7/2010 |
| WO | 2013160875 A1 | 10/2013 |

OTHER PUBLICATIONS

Escribano et al., Chem Med Chem 2011, 6, 2252-2263.*
Voight, E. et al., "Targeted-Directed Synthesis of Antibacterial Drug Candidate GSK966587," Organic Letters (2010), vol. 12, No. 15, pp. 3422-3425.

* cited by examiner

*Primary Examiner* — Niloofar Rahmani
(74) *Attorney, Agent, or Firm* — Hunton & Williams LLP

(57) ABSTRACT

The invention relates to a process and synthetic intermediates that can be used for manufacturing the compound of formula (1-6) which is a synthetic intermediate useful in the preparation of antibiotic compounds.

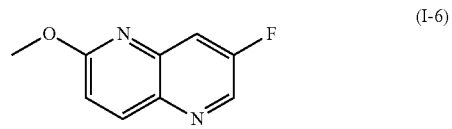

(I-6)

8 Claims, No Drawings

PROCESS FOR MANUFACTURING A NAPHTHYRIDINE DERIVATIVE

CROSS-REFERENCE TO RELATED APPLICATIONS

This application is the U.S. National Phase of International Patent Application No. PCT/IB2013/051044, filed Feb. 8, 2013, which claims the benefit of priority to International Patent Application No. PCT/IB2012/050609, filed Feb. 10, 2012, the contents of each are hereby incorporated by reference in their entireties.

The present invention relates to a new process for manufacturing known intermediates in the preparation of antibiotic compounds, as well as to new synthetic intermediates.

The compound of formula I-6

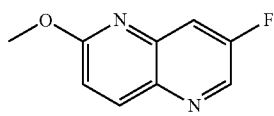

I-6 is a synthetic intermediate useful in the preparation of antibiotic compounds. The use of such a synthetic intermediate for preparing antibiotic compounds is for example disclosed generically or specifically in WO 2004/087467, WO 2005/097781, WO 2008/009700, WO 2010/067332 or WO 2010/084152.

The known methods for preparing the compound of formula I-6 are however not most appropriate for large manufacturing, notably because of:

the costs of the starting materials, and/or the use of toxic metals, and/or the use of expensive catalysts or reaction conditions, and/or moderate yields.

The Applicants have now found an improved manufacturing route to obtain the compound of formula I-6, which uses the new intermediates of formulae I-3 and 1-4 below

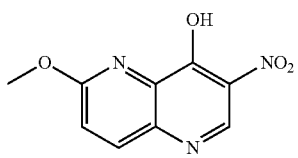

I-3

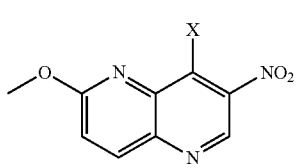

I-4

Said manufacturing route starts from the already known (and commercially available) compound of formula I-1

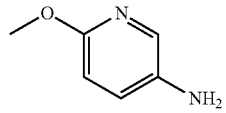

I-1

Various embodiments of the invention are presented hereafter:

1) The invention firstly relates to a new synthetic intermediate in the preparation of the compound of formula I-6 described previously, namely the compound of formula I-3

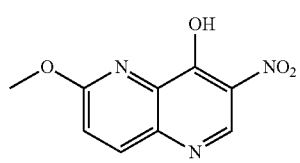

I-3 or to a salt of that compound.

2) The invention also relates to a process for manufacturing the compound of formula I-3 as defined in embodiment 1), said process comprising the reaction of the compound of formula I-2

I-2 with a nitration reagent or mixture of reagents at a temperature from 20° C. to 100° C.

3) Preferably, the reaction of the process of embodiment 2) will be performed at a temperature from 50° C. to 70° C. (and in particular at a temperature of about 60° C.).

4) Preferably, the reaction of the process of embodiment 2) or 3) will be performed using nitric acid having a concentration of at least 65% in weight (and more preferably a concentration over 70% in weight).

5) In a particularly preferred manner, the reaction of the process according to embodiment 4) will be performed in the absence of sulfuric acid.

6) The reaction of the process according to embodiment 4) or 5) will notably be performed using fuming nitric acid.

7) Preferably, the compound of formula I-2 used in the process according to one of embodiments 2) to 6) will be obtained by a) reacting of the compound of formula I-1 below

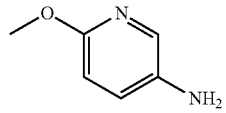

I-1 with 2,2-dimethyl-1,3-dioxane-4,6-dione and triethylorthoformate in an alkanol, in a mixture of at least two alkanols or in a mixture of solvents comprising at least one polar aprotic solvent and at least one alkanol (and preferably at least one ($C_1$-$C_4$)-alkanol); and b) heating the intermediate obtained after step a) in a solvent or mixture of solvents.

8) Preferably, the reaction of step a) of the process according to embodiment 7) will be performed in ethanol or in a mixture of solvents comprising ethanol (and in particular in ethanol).

9) Preferably, the process according to embodiment 7) or 8) will be such that the reaction of its step a) is performed at a temperature between 50° C. and the reflux temperature of the reaction mixture (and in particular at a temperature between 65° C. and the reflux temperature of the reaction mixture).

10) Step a) of the process according to any of embodiments 7) to 9) will preferably be performed using from 1 to 1.4 equivalents of 2,2-dimethyl-1,3-dioxane-4,6-dione per equivalent of compound of formula I-1 and from 1 to 1.2 equivalents of triethylorthoformate per equivalent of compound of formula I-1, and notably using from 1.1 to 1.3 equivalents of 2,2-dimethyl-1,3-dioxane-4,6-dione per equivalent of compound of formula I-1 and from 1.05 to 1.15 equivalents of triethylorthoformate per equivalent of compound of formula I-1.

11) Preferably, the reaction of step b) of the process according to one of embodiments 7) to 10) will be performed in a solvent or a mixture of solvents which has a boiling point higher than 180° C. (and preferably a boiling point higher than 200° C. or even higher than 220° C.).

12) Preferably, the solvent or a mixture of solvents of step b) of the process according to embodiment 11) will comprise (and notably consist in) a mixture of 1,1'-biphenyl and phenoxybenzene, or a mixture of 1,1'-biphenyl, phenoxybenzene and 1,3-dimethyl-imidazolidinone.

13) The invention furthermore relates to the use of the compound of formula I-2 as defined in embodiment 2), or a salt thereof, in a process for manufacturing the compound of formula I-5

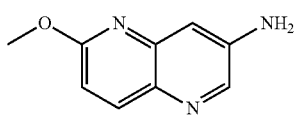

or a salt thereof.

14) The invention furthermore relates to the use of the compound of formula I-2 as defined in embodiment 2), or a salt thereof, in a process for manufacturing the compound of formula I-6

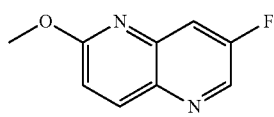

or a salt thereof.

15) The invention furthermore relates to the use of the compound of formula I-3 as defined in embodiment 1), or a salt thereof, in a process for manufacturing the compound of formula I-5 as defined in embodiment 13) or a salt thereof.

16) The invention furthermore relates to the use of the compound of formula I-3 as defined in embodiment 1), or a salt thereof, in a process for manufacturing the compound of formula I-6 as defined in embodiment 14) or a salt thereof.

17) The invention also relates a compound of formula I-4

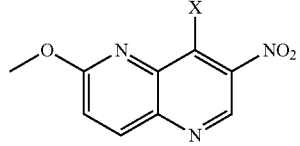

wherein X is Br or Cl;
or to a salt of such a compound.

18) According to a particular variant of embodiment 17), the compound of formula I-4 or its salt will be such that X is Br.

19) According to another particular variant of embodiment 17), the compound of formula I-4 or its salt will be such that X is Cl.

20) The invention further relates to the use of the compound of formula I-3 as defined in embodiment 1) in a process for manufacturing the compound of formula I-4 as defined in one of embodiments 17) to 19) or a salt thereof.

21) The invention furthermore relates to a process for manufacturing the compound of formula I-4 as defined in embodiment 17), or a salt thereof, said process comprising the reaction of the compound of formula I-3 as defined in embodiment 1) with pentachlorophosphorane, tribromophosphine, trichlorophosphine, phosphoryl tribromide or phosphoryl trichloride (and preferably with tribromophosphine or phosphoryl trichloride).

22) According to a sub-embodiment of embodiment 21), the process of embodiment 21) will be such that it comprises the reaction of the compound of formula I-3 as defined in embodiment 1) with tribromophosphine or phosphoryl tribromide (and preferably with tribromophosphine) in a polar aprotic solvent or a polar aprotic mixture of solvents, whereby the compound of formula I-4 as defined in embodiment 18) will be obtained.

23) According to another sub-embodiment of embodiment 21), the process of embodiment 21) will be such that it comprises the reaction of the compound of formula I-3 as defined in embodiment 1) with pentachlorophosphorane, trichlorophosphine or phosphoryl trichloride (and preferably with phosphoryl trichloride) in a polar aprotic solvent or a polar aprotic mixture of solvents, whereby the compound of formula I-4 as defined in embodiment 19) will be obtained.

24) According to one particular variant of the process of any of embodiments 21) to 23), the reaction involving the compound of formula I-3 will be performed in the absence of solvent (that is, in neat conditions).

25) According to another particular variant of the process of any of embodiments 21) to 23), the reaction involving the compound of formula I-3 will be performed in a polar aprotic solvent or a polar aprotic mixture of solvents.

26) Preferably, the manufacturing process of embodiment 25) will be performed in DMF or a polar aprotic mixture of solvents comprising DMF (in particular in DMF).

27) Preferably, in the manufacturing process of embodiment 25) or 26), the polar aprotic solvent or polar aprotic mixture of solvents will be heated at a temperature of at least 40 or 65° C. for a period of at least 30 min.

28) The manufacturing process according to any of embodiments 21) to 27) will preferably be performed using from 1 to 2.2 equivalents of pentachlorophosphorane, tribromophosphine, trichlorophosphine, phosphoryl tribromide or phosphoryl trichloride per equivalent of compound of formula I-3, and notably using from 1.1 to 2 equivalents of pentachlorophosphorane, tribromophosphine, trichlorophosphine, phosphoryl tribromide or phosphoryl trichloride per equivalent of compound of formula I-3.

29) The invention further relates to the use of the compound of formula I-4 as defined in one of embodiments 17) to 19) in a process for manufacturing the compound of formula I-5 as defined in embodiment 13), or a salt thereof.

30) The invention also relates to a process for manufacturing the compound of formula I-5 as defined in embodiment 13), said process comprising the reaction of the compound of formula I-4 as defined in one of embodiments 17) to 19) with hydrogen in an alkanol in the presence of a base and of a catalyst selected from Raney nickel, iron, palladium and platinum (the catalyst being preferably Raney nickel).

31) According to a preferred sub-embodiment of embodiment 30), the base will be selected from TEA, DBU, NaOEt, NaOMe, tBuOK, $K_2CO_3$, $Na_2CO_3$, NaOH, KOH, LiOH and a mixture of at least two of the latter (and will in particular be TEA).

32) Preferably, the manufacturing process of embodiment 30) or 31) will be such that the base is added in two or more portions (that is, stepwise).

33) Preferably, the alkanol in the manufacturing process according to any of embodiments 30) to 32) will be selected from MeOH, EtOH, iPrOH and a mixture of at least two of the latter (and will preferably be MeOH).

34) The process according to any of embodiments 30) to 33) will preferably be performed using from 1.5 to 2.5 equivalents of base per equivalent of compound of formula I-4, and notably using from 1.8 to 2.2 equivalents of base per equivalent of compound of formula I-4 (for example about 2 equivalents of TEA per equivalent of compound of formula I-4).

35) The invention also relates to a process for manufacturing the compound of formula I-6 as defined in embodiment 14), said process comprising:
a) reacting the compound of formula I-5 as defined at embodiment 13) with a couple of reagents consisting of a fluorination reagent and a nitrite reagent, and
b) heating the diazonium salt obtained after step a).

36) According to one variant of the process of embodiment 35), step a) will be performed in an aqueous medium.

37) Preferably, in the process according to embodiment 36), the couple of reagents consisting of a fluorination reagent and a nitrite reagent will be one of the following combinations of reagents:
  $HBF_4$ and $NaNO_2$ or $KNO_2$;
  $HPF_6$ and $NaNO_2$ or $KNO_2$;
  $NaNO_2$ or $KNO_2$ in the presence of aqueous HCl and $NaBF_4$ or $HBF_4$; or
  $HBF_4$ and $NaNO_2$ or $KNO_2$.

38) Preferably, the process of embodiment 36) or 37) will be such that the diazonium salt obtained after step a) is isolated prior to performing step b).

39) Preferably also, the process according to one of embodiments 36) to 38) will be such that, in step b), either the diazonium salt is heated in an inert solvent selected from the group consisting of Hept, Hex, MeCHex, toluene, chlorobenzene, decaline and mixture of two or more of the latter, or the diazonium salt is heated neat or in sand.

40) In particular, the process according to embodiment 39) will be such that, in step b), the diazonium salt is heated in Hept.

41) According to another variant of the process of embodiment 35), step a) will be performed in non-aqueous conditions.

42) According to one sub-variant of the process of embodiment 41), step a) will be performed in a polar aprotic solvent or a polar aprotic mixture of solvents.

43) Preferably, in the process according to embodiment 42), the couple of reagents consisting of a fluorination reagent and a nitrite reagent will be one of the following combinations of reagents:
  boron trifluoride diethyl etherate and an alkyl nitrite selected from n-butyl nitrite, tert-butyl nitrite, n-pentyl nitrite, iso-pentyl nitrite and tert-pentyl nitrite;
  $NOBF_4$; or
  $NOPF_6$.

44) Preferably, in the process according to embodiment 42) or 43), the polar aprotic solvent or polar aprotic mixture of solvents will be DCM, THF, diethyl ether, dimethoxyethane (and in particular THF), or a mixture of two or more of the latter.

45) In particular, the process according to one of embodiments 42) to 44) will comprise reacting the compound of formula I-5 with boron trifluoride diethyl etherate and tert-butyl nitrite in THF.

46) According to another sub-variant of the process of embodiment 41), step a) will be performed using liquid HF as solvent.

47) Preferably, in the process according to embodiment 46), the couple of reagents consisting of a fluorination reagent and a nitrite reagent will be one of the following combinations of reagents:
  HF in the presence of Pyr and $NaNO_2$ or $KNO_2$; or
  HF and $N_2O_4$.

48) In particular, the process according to embodiment 46) or 47) will comprise reacting the compound of formula I-5 with Pyr and $NaNO_2$ or $KNO_2$ in liquid HF followed by heating the reaction mixture (no isolation of the intermediate diazonium salt being performed).

49) Preferably, the manufacturing process according to any of embodiments 35) to 48) will be performed using at least 1.5 equivalents of fluorination reagent per equivalent of compound of formula I-5 and from 1 to 1.2 equivalents of nitrite reagent per equivalent of compound of formula I-5, and notably using at least 2 equivalents of fluorination reagent per equivalent of compound of formula I-5 and from 1.05 to 1.15 equivalents of nitrite reagent per equivalent of compound of formula I-5.

50) Preferably, in the manufacturing process according to any of embodiments 35) to 49), step a) will be performed at a temperature below 0° C. (and in particular at a temperature below −10° C.).

51) Preferably, in step b) of the manufacturing process according to any of embodiments 35) to 50), the diazonium salt will be heated in step b) to a temperature above 20° C. (and in particular at a temperature of at least 50 or 60° C.).

52) In particular, the process according to embodiment 35) will consist in reacting the compound of formula I-5 with hydrogen fluoride in the presence of Pyr, reacting the intermediate thus obtained with sodium nitrite and heating the reaction mixture at a temperature of at least 50° C.

53) The invention also relates to a process for manufacturing the compound of formula I-6 as defined in embodiment 14) or a salt thereof, said process comprising the following steps:
a) performing a manufacturing process according to one of embodiments 30) to 34) to obtain the compound of formula I-5 as defined in embodiment 13) or a salt thereof, and b) performing a manufacturing process according to one of embodiments 35) to 52) to obtain the compound of formula I-6 as defined in embodiment 14) or a salt thereof.

54) The invention moreover relates to the use of the compound of formula I-4 as defined in embodiment 17) or a salt thereof in a process for manufacturing the compound of formula I-6 as defined in embodiment 14) or a salt thereof.

55) The invention besides relates to a process for manufacturing the compound of formula I-6 as defined in embodiment 14) or a salt thereof, which process comprises the following steps:
a) performing a process according to one of embodiments 2) to 12) to obtain the compound of formula I-3 as defined in embodiment 1) or a salt thereof;
b) performing a process according to one of embodiments 21) to 28) to obtain the compound of formula I-4 as defined in one of embodiments 17) to 19) or a salt thereof;
c) performing a process according to one of embodiments 30) to 34) to obtain the compound of formula I-5 as defined in embodiment 13) or a salt thereof;
d) performing a process according to one of embodiments 35) to 52) to obtain the compound of formula I-6 as defined in embodiment 14) or a salt thereof.

This invention thus notably relates to the compounds, manufacturing processes and uses as defined in one of embodiments 1), 2), 13) to 17), 20), 29), 30), 35) and 53) to 55), or to these compounds, manufacturing processes and uses further limited under consideration of their respective dependencies by the characteristics of any one of embodiments 3) to 12), 18), 19), 21) to 28), 31) to 34) and 36) to 52). In particular, based on the dependencies of the different embodiments as disclosed hereinabove, the following manufacturing process and use embodiments are thus possible and intended and herewith specifically disclosed in individualized form:

1, 2, 3+2, 4+2, 4+3+2, 5+4+2, 5+4+3+2, 6+4+2, 6+4+3+2, 6+5+4+2, 6+5+4+3+2, 7+2, 7+3+2, 7+4+2, 7+4+3+2, 7+5+4+2, 7+5+4+3+2, 7+6+4+2, 7+6+4+3+2, 7+6+5+4+2, 7+6+5+4+3+2, 8+7+2, 8+7+3+2, 8+7+4+2, 8+7+4+3+2, 8+7+5+4+2, 8+7+5+4+3+2, 8+7+6+4+2, 8+7+6+4+3+2, 8+7+6+5+4+2, 8+7+6+5+4+3+2, 9+7+2, 9+7+3+2, 9+7+4+2, 9+7+4+3+2, 9+7+5+4+2, 9+7+5+4+3+2, 9+7+6+4+2, 9+7+6+4+3+2, 9+7+6+5+4+2, 9+7+6+5+4+3+2, 9+8+7+2, 9+8+7+3+2, 9+8+7+4+2, 9+8+7+4+3+2, 9+8+7+5+4+2, 9+8+7+5+4+3+2, 9+8+7+6+4+2, 9+8+7+6+4+3+2, 9+8+7+6+5+4+2, 9+8+7+6+5+4+3+2, 10+7+2, 10+7+3+2, 10+7+4+2, 10+7+4+3+2, 10+7+5+4+2, 10+7+5+4+3+2, 10+7+6+4+2, 10+7+6+4+3+2, 10+7+6+5+4+2, 10+7+6+5+4+3+2, 10+8+7+2, 10+8+7+3+2, 10+8+7+4+2, 10+8+7+4+3+2, 10+8+7+5+4+2, 10+8+7+5+4+3+2, 10+8+7+6+4+2, 10+8+7+6+4+3+2, 10+8+7+6+5+4+2, 10+8+7+6+5+4+3+2, 10+9+7+2, 10+9+7+3+2, 10+9+7+4+2, 10+9+7+4+3+2, 10+9+7+5+4+2, 10+9+7+5+4+3+2, 10+9+7+6+4+2, 10+9+7+6+4+3+2, 10+9+7+6+5+4+2, 10+9+7+6+5+4+3+2, 10+9+8+7+2, 10+9+8+7+3+2, 10+9+8+7+4+2, 10+9+8+7+4+3+2, 10+9+8+7+5+4+2, 10+9+8+7+5+4+3+2, 10+9+8+7+6+4+2, 10+9+8+7+6+4+3+2, 10+9+8+7+6+5+4+2, 10+9+8+7+6+5+4+3+2, 11+7+2, 11+7+3+2, 11+7+4+2, 11+7+4+3+2, 11+7+5+4+2, 11+7+5+4+3+2, 11+7+6+4+2, 11+7+6+4+3+2, 11+7+6+5+4+2, 11+7+6+5+4+3+2, 11+8+7+2, 11+8+7+3+2, 11+8+7+4+2, 11+8+7+4+3+2, 11+8+7+5+4+2, 11+8+7+5+4+3+2, 11+8+7+6+4+2, 11+8+7+6+4+3+2, 11+8+7+6+5+4+2, 11+8+7+6+5+4+3+2, 11+9+7+2, 11+9+7+3+2, 11+9+7+4+2, 11+9+7+4+3+2, 11+9+7+5+4+2, 11+9+7+5+4+3+2, 11+9+7+6+4+2, 11+9+7+6+4+3+2, 11+9+7+6+5+4+2, 11+9+7+6+5+4+3+2, 11+9+8+7+2, 11+9+8+7+3+2, 11+9+8+7+4+2, 11+9+8+7+4+3+2, 11+9+8+7+5+4+2, 11+9+8+7+5+4+3+2, 11+9+8+7+6+4+2, 11+9+8+7+6+4+3+2, 11+9+8+7+6+5+4+2, 11+9+8+7+6+5+4+3+2, 11+10+7+2, 11+10+7+3+2, 11+10+7+4+2, 11+10+7+4+3+2, 11+10+7+5+4+2, 11+10+7+5+4+3+2, 11+10+7+6+4+2, 11+10+7+6+4+3+2, 11+10+7+6+5+4+2, 11+10+7+6+5+4+3+2, 11+10+8+7+2, 11+10+8+7+3+2, 11+10+8+7+4+2, 11+10+8+7+4+3+2, 11+10+8+7+5+4+2, 11+10+8+7+5+4+3+2, 11+10+8+7+6+4+2, 11+10+8+7+6+4+3+2, 11+10+8+7+6+5+4+2, 11+10+8+7+6+5+4+3+2, 11+10+9+7+2, 11+10+9+7+3+2, 11+10+9+7+4+2, 11+10+9+7+4+3+2, 11+10+9+7+5+4+2, 11+10+9+7+5+4+3+2, 11+10+9+7+6+4+2, 11+10+9+7+6+4+3+2, 11+10+9+7+6+5+4+2, 11+10+9+7+6+5+4+3+2, 11+10+9+8+7+2, 11+10+9+8+7+3+2, 11+10+9+8+7+4+2, 11+10+9+8+7+4+3+2, 11+10+9+8+7+5+4+2, 11+10+9+8+7+5+4+3+2, 11+10+9+8+7+6+4+2, 11+10+9+8+7+6+4+3+2, 11+10+9+8+7+6+5+4+2, 11+10+9+8+7+6+5+4+3+2, 12+11+7+2, 12+11+7+3+2, 12+11+7+4+2, 12+11+7+4+3+2, 12+11+7+5+4+2, 12+11+7+5+4+3+2, 12+11+7+6+4+2, 12+11+7+6+4+3+2, 12+11+7+6+5+4+2, 12+11+7+6+5+4+3+2, 12+11+8+7+2, 12+11+8+7+3+2, 12+11+8+7+4+2, 12+11+8+7+4+3+2, 12+11+8+7+5+4+2, 12+11+8+7+5+4+3+2, 12+11+8+7+6+4+2, 12+11+8+7+6+4+3+2, 12+11+8+7+6+5+4+2, 12+11+8+7+6+5+4+3+2, 12+11+9+7+2, 12+11+9+7+3+2, 12+11+9+7+4+2, 12+11+9+7+4+3+2, 12+11+9+7+5+4+2, 12+11+9+7+5+4+3+2, 12+11+9+7+6+4+2, 12+11+9+7+6+4+3+2, 12+11+9+7+6+5+4+2, 12+11+9+7+6+5+4+3+2, 12+11+9+8+7+2, 12+11+9+8+7+3+2, 12+11+9+8+7+4+2, 12+11+9+8+7+4+3+2, 12+11+9+8+7+5+4+2, 12+11+9+8+7+5+4+3+2, 12+11+9+8+7+6+4+2, 12+11+9+8+7+6+4+3+2, 12+11+9+8+7+6+5+4+2, 12+11+9+8+7+6+5+4+3+2, 12+11+10+7+2, 12+11+10+7+3+2, 12+11+10+7+4+2, 12+11+10+7+4+3+2, 12+11+10+7+5+4+2, 12+11+10+7+5+4+3+2, 12+11+10+7+6+4+2, 12+11+10+7+6+4+3+2, 12+11+10+7+6+5+4+2, 12+11+10+7+6+5+4+3+2, 12+11+10+8+7+2, 12+11+10+8+7+3+2, 12+11+10+8+7+4+2, 12+11+10+8+7+4+3+2, 12+11+10+8+7+5+4+2, 12+11+10+8+7+5+4+3+2, 12+11+10+8+7+6+4+2, 12+11+10+8+7+6+4+3+2, 12+11+10+8+7+6+5+4+2, 12+11+10+8+7+6+5+4+3+2, 12+11+10+9+7+2, 12+11+10+9+7+3+2, 12+11+10+9+7+4+2, 12+11+10+9+7+4+3+2, 12+11+10+9+7+5+4+2, 12+11+10+9+7+5+4+3+2, 12+11+10+9+7+6+4+2, 12+11+10+9+7+6+4+3+2, 12+11+10+9+7+6+5+4+2, 12+11+10+9+7+6+5+4+3+2, 12+11+10+9+8+7+2, 12+11+10+9+8+7+3+2, 12+11+10+9+8+7+4+2, 12+11+10+9+8+7+4+3+2, 12+11+10+9+8+7+5+4+2, 12+11+10+9+8+7+5+4+3+2, 12+11+10+9+8+7+6+4+2, 12+11+10+9+8+7+6+4+3+2, 12+11+10+9+8+7+6+5+4+2, 12+11+10+9+8+7+6+5+4+3+2, 13, 14, 15, 16, 17, 18+17, 19+17, 20+17, 20+18+17, 20+19+17, 21, 22+21, 23+21, 24+21, 24+22+21, 24+23+21, 25+21, 25+22+21, 25+23+21, 26+25+21, 26+25+22+21, 26+25+23+21, 27+25+21, 27+25+22+21, 27+25+23+21, 27+26+25+21, 27+26+25+22+21, 27+26+25+23+21, 28+21, 28+22+21, 28+23+21, 28+24+21, 28+24+22+21, 28+24+23+21, 28+25+21, 28+25+22+21, 28+25+23+21, 28+26+25+21, 28+26+25+22+21, 28+26+25+23+21, 28+27+25+21, 28+27+25+22+21, 28+27+25+23+21, 28+27+26+25+21, 28+27+26+25+22+21, 28+27+26+25+23+21, 29+17, 29+18+17, 29+19+17, 30+17, 30+18+17, 30+19+17, 31+30+17, 31+30+18+17, 31+30+19+17, 32+30+17, 32+30+18+17, 32+30+19+17, 32+31+30+17, 32+31+30+18+17, 32+31+30+19+17, 33+30+17, 33+30+18+17, 33+30+19+17, 33+31+30+17, 33+31+30+18+17, 33+31+30+19+17, 33+32+30+17,

33+32+30+18+17, 33+32+30+19+17, 33+32+31+30+17, 33+32+31+30+18+17, 33+32+31+30+19+17, 34+30+17, 34+30+18+17, 34+30+19+17, 34+31+30+17, 34+31+30+18+17, 34+31+30+19+17, 34+32+30+17, 34+32+30+18+17, 34+32+30+19+17, 34+32+31+30+17, 34+32+31+30+18+17, 34+32+31+30+19+17, 34+33+30+17, 34+33+30+18+17, 34+33+30+19+17, 34+33+31+30+17, 34+33+31+30+18+17, 34+33+31+30+19+17, 34+33+32+30+17, 34+33+32+30+18+17, 34+33+32+30+19+17, 34+33+32+31+30+17, 34+33+32+31+30+18+17, 34+33+32+31+30+19+17, 35, 36+35, 37+36+35, 38+36+35, 38+37+36+35, 39+36+35, 39+37+36+35, 39+38+36+35, 39+38+37+36+35, 40+39+36+35, 40+39+37+36+35, 40+39+38+36+35, 40+39+38+37+36+35, 41+35, 42+41+35, 43+42+41+35, 44+42+41+35, 44+43+42+41+35, 45+42+41+35, 45+43+42+41+35, 45+44+42+41+35, 45+44+43+42+41+35, 46+41+35, 47+46+41+35, 48+46+41+35, 48+47+46+41+35, 49+35, 49+36+35, 49+37+36+35, 49+38+36+35, 49+38+37+36+35, 49+39+36+35, 49+39+37+36+35, 49+39+38+36+35, 49+39+38+37+36+35, 49+40+39+36+35, 49+40+39+37+36+35, 49+40+39+38+36+35, 49+40+39+38+37+36+35, 49+41+35, 49+42+41+35, 49+43+42+41+35, 49+44+42+41+35, 49+44+43+42+41+35, 49+45+42+41+35, 49+45+43+42+41+35, 49+45+44+42+41+35, 49+45+44+43+42+41+35, 49+46+41+35, 49+47+46+41+35, 49+48+46+41+35, 49+48+47+46+41+35, 50+35, 50+36+35, 50+37+36+35, 50+38+36+35, 50+38+37+36+35, 50+39+36+35, 50+39+37+36+35, 50+39+38+36+35, 50+39+38+37+36+35, 50+40+39+36+35, 50+40+39+37+36+35, 50+40+39+38+36+35, 50+40+39+38+37+36+35, 50+41+35, 50+42+41+35, 50+43+42+41+35, 50+44+42+41+35, 50+44+43+42+41+35, 50+45+42+41+35, 50+45+43+42+41+35, 50+45+44+42+41+35, 50+45+44+43+42+41+35, 50+46+41+35, 50+47+46+41+35, 50+48+46+41+35, 50+48+47+46+41+35, 50+49+35, 50+49+36+35, 50+49+37+36+35, 50+49+38+36+35, 50+49+38+37+36+35, 50+49+39+36+35, 50+49+39+37+36+35, 50+49+39+38+36+35, 50+49+39+38+37+36+35, 50+49+40+39+36+35, 50+49+40+39+37+36+35, 50+49+40+39+38+36+35, 50+49+40+39+38+37+36+35, 50+49+41+35, 50+49+42+41+35, 50+49+43+42+41+35, 50+49+44+42+41+35, 50+49+44+43+42+41+35, 50+49+45+42+41+35, 50+49+45+43+42+41+35, 50+49+45+44+42+41+35, 50+49+45+44+43+42+41+35, 50+49+46+41+35, 50+49+47+46+41+35, 50+49+48+46+41+35, 50+49+48+47+46+41+35, 51+35, 51+36+35, 51+37+36+35, 51+38+36+35, 51+38+37+36+35, 51+39+36+35, 51+39+37+36+35, 51+39+38+36+35, 51+39+38+37+36+35, 51+40+39+36+35, 51+40+39+37+36+35, 51+40+39+38+36+35, 51+40+39+38+37+36+35, 51+41+35, 51+42+41+35, 51+43+42+41+35, 51+44+42+41+35, 51+44+43+42+41+35, 51+45+42+41+35, 51+45+43+42+41+35, 51+45+44+42+41+35, 51+45+44+43+42+41+35, 51+46+41+35, 51+47+46+41+35, 51+48+46+41+35, 51+48+47+46+41+35, 51+49+35, 51+49+36+35, 51+49+37+36+35, 51+49+38+36+35, 51+49+38+37+36+35, 51+49+39+36+35, 51+49+39+37+36+35, 51+49+39+38+36+35, 51+49+39+38+37+36+35, 51+49+40+39+36+35, 51+49+40+39+37+36+35, 51+49+40+39+38+36+35, 51+49+40+39+38+37+36+35, 51+49+41+35, 51+49+42+41+35, 51+49+43+42+41+35, 51+49+44+42+41+35, 51+49+44+43+42+41+35, 51+49+45+42+41+35, 51+49+45+43+42+41+35, 51+49+45+44+42+41+35, 51+49+45+44+43+42+41+35, 51+49+46+41+35, 51+49+47+46+41+35, 51+49+48+46+41+35, 51+49+48+47+46+41+35, 51+50+35, 51+50+36+35, 51+50+37+36+35, 51+50+38+36+35, 51+50+38+37+36+35, 51+50+39+36+35, 51+50+39+37+36+35, 51+50+39+38+36+35, 51+50+39+38+37+36+35, 51+50+40+39+36+35, 51+50+40+39+37+36+35, 51+50+40+39+38+36+35, 51+50+40+39+38+37+36+35, 51+50+41+35, 51+50+42+41+35, 51+50+43+42+41+35, 51+50+44+42+41+35, 51+50+44+43+42+41+35, 51+50+45+42+41+35, 51+50+45+43+42+41+35, 51+50+45+44+42+41+35, 51+50+45+44+43+42+41+35, 51+50+46+41+35, 51+50+47+46+41+35, 51+50+48+46+41+35, 51+50+48+47+46+41+35, 51+50+49+35, 51+50+49+36+35, 51+50+49+37+36+35, 51+50+49+38+36+35, 51+50+49+38+37+36+35, 51+50+49+39+36+35, 51+50+49+39+37+36+35, 51+50+49+39+38+36+35, 51+50+49+39+38+37+36+35, 51+50+49+40+39+36+35, 51+50+49+40+39+37+36+35, 51+50+49+40+39+38+36+35, 51+50+49+40+39+38+37+36+35, 51+50+49+41+35, 51+50+49+42+41+35, 51+50+49+43+42+41+35, 51+50+49+44+42+41+35, 51+50+49+44+43+42+41+35, 51+50+49+45+42+41+35, 51+50+49+45+43+42+41+35, 51+50+49+45+44+42+41+35, 51+50+49+45+44+43+42+41+35, 51+50+49+46+41+35, 51+50+49+47+46+41+35, 51+50+49+48+46+41+35, 51+50+49+48+47+46+41+35, 52+35, 53, 54, 55

In the list above, the numbers refer to the embodiments according to their numbering provided hereinabove whereas "+" indicates the dependency from another embodiment. The different individualised embodiments are separated by commas. In other words, "5+4+2" for example refers to embodiment 5) depending on embodiment 4), depending on embodiment 2), i.e. embodiment "5+4+1" corresponds to embodiment 2) further limited by the features of embodiments 4) and 5). Likewise, "11+9+7+2" refers to embodiment 11) depending mutatis mutandis on embodiments 9) and 7), depending on embodiment 2), i.e. embodiment "11+9+7+2" corresponds to embodiment 2) further limited by the features of embodiment 7), further limited by the features of embodiments 9) and 11).

ABBREVIATIONS AND TERMS USED IN THIS TEXT

Abbreviations

The following abbreviations are used throughout the specification and the examples:
Ac acetyl
aq. aqueous
CHex cyclohexane
DCM dichloromethane
DIPEA N,N-diisopropylethylamine
DMAC dimethylacetamide
DME 1,2-dimethoxyethane
DMF dimethylformamide
DMPU 1,3-dimethyl-3,4,5,6-tetrahydro-2(1H)-pyrimidinone DMSO dimethylsulfoxide
d6-DMSO perdeuterated dimethylsulfoxide
EA ethyl acetate
eq. equivalent(s)
Et ethyl
ET external temperature
Hept heptane
Hex hexane
iPr iso-propyl
IT internal temperature
LC-MS liquid chromatography-mass spectroscopy
MS mass spectroscopy
MeCHex methylcyclohexane
MeCN acetonitrile
mol % percent in moles
NMP N-methylpyrrolidone
org. organic
Pyr pyridine
% a/a percent determined by area ratio
% w/w percent determined by weight ratio
RT room temperature
sat. saturated
TBME tert-butyl methyl ether
tBu tert-butyl
TFA trifluoroacetic acid
TEA triethylamine
THF tetrahydrofurane
$t_R$ retention time

DEFINITIONS OF PARTICULAR TERMS USED IN THIS TEXT

The following paragraphs provide definitions of the various chemical moieties for the compounds according to the invention as well as other particular terms used in this text and are intended to apply uniformly throughout the specification and claims, unless an otherwise expressly set out definition provides a broader or narrower definition:

The expression "nitration reagent or mixture of reagents" refers to a reagent or a mixture of reagents selected from nitric acid, a mixture of nitric acid and sulfuric acid, and a mixture of one or more of $NaNO_3$, $NaNO_3$ or $CuNO_3$ with one or more acids selected from hydrochloric acid, hydrobromic acid, sulfuric acid and nitric acid.

The expression "polar aprotic solvent" refers to a solvent which does not display hydrogen bonding, does not have an acidic hydrogen but is able to stabilise ions. Representative examples of polar aprotic solvents include DCM, MeCN, EA, iPrOAc, THF, 2-methyl-tetrahydrofurane, DMAC, DME, DMF, DMSO, dioxane, diethyl ether, NMP, TBME or cyclopentyl methyl ether.

The expression "polar aprotic mixture of solvents" refers to a mixture of solvents which includes at least one polar aprotic solvent as previously defined and at least another aprotic solvent (which may be polar or apolar). Representative examples of polar aprotic mixtures of solvents include, but are not limited to: a mixture of two solvents selected from the group consisting of DCM, MeCN, EA, iPrOAc, THF, 2-methyl-tetrahydrofurane, DMAC, DME, DMF, DMSO, dioxane, diethyl ether, NMP, TBME and cyclopentyl methyl ether; a mixture of toluene with one or more of DCM, MeCN, EA, iPrOAc, THF, 2-methyl-tetrahydrofurane, DMAC, DME, DMF, DMSO, dioxane, diethyl ether, NMP, TBME or cyclopentyl methyl ether; a mixture of Hex with one or more of DCM, MeCN, EA, iPrOAc, THF, 2-methyl-tetrahydrofurane, DMAC, DME, DMF, DMSO, dioxane, diethyl ether, TBME or cyclopentyl methyl ether; a mixture of Hept with one or more of DCM, MeCN, EA, iPrOAc, THF, 2-methyl-tetrahydrofurane, DMAC, DME, DMF, DMSO, dioxane, diethyl ether, TBME or cyclopentyl methyl ether; and a mixture of toluene with Hex, cHex, MeCHex or Hept and one or more of DCM, MeCN, EA, iPrOAc, THF, 2-methyl-tetrahydrofurane, DMAC, DME, DMF, DMSO, dioxane, diethyl ether, TBME or cyclopentyl methyl ether.

By "a solvent or a mixture of solvents which has a boiling point higher than 180° C." is understood a solvent or a mixture of solvents which has a boiling point higher than 180° C. at a pressure of 1013 mbar. Examples of solvents or mixtures of solvents which has a boiling point higher than 180° C. include, but are not limited to, octadec-1-ene, DMPU, a mixture of 1,1'-biphenyl and phenoxybenzene, or a mixture of 1,1'-biphenyl, phenoxybenzene and 1,3-dimethyl-imidazolidinone.

The term "alkanol" refers to an aliphatic primary, secondary or tertiary alcohol containing from one to six carbon atoms and one hydroxy group. The term "$(C_1-C_x)$alkanol" refers to an aliphatic primary, secondary or tertiary alcohol containing 1 to x carbon atoms and one hydroxyl group. Examples of alkanols include methanol, ethanol and isopropanol.

The expression "couple of reagents consisting of a fluorination reagent and an nitrite reagent" refers specifically to one of the following reagents or combinations of reagents:
$HBF_4$ and $NaNO_2$ or $KNO_2$;
$HPF_6$ and $NaNO_2$ or $KNO_2$;
$NaBF_4$ and $NaNO_2$ or $KNO_2$;
$HBF_4$ and $NaNO_2$ or $KNO_2$;
boron trifluoride diethyl etherate and an alkyl nitrite selected from n-butyl nitrite, tert-butyl nitrite, n-pentyl nitrite, iso-pentyl nitrite and tert-pentyl nitrite;
pyridinium fluoride and $NaNO_2$ or $KNO_2$;
$NOBF_4$;
$NOPF_6$; or
HF and $N_2O_4$.

The expression "room temperature" as used herein refers to a temperature of from 20 to 30° C., and preferably 25° C.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

Particular embodiments of the invention are described in the following Examples, which serve to illustrate the invention in more detail without limiting its scope in any way.

EXAMPLES

All temperatures given are external temperatures and are stated in ° C. Compounds were characterized by $^1$H-NMR (400 MHz) or $^{13}$C-NMR (100 MHz) (Bruker; chemical shifts δ are given in ppm relative to the solvent used; multiplicities: s=singlet, d=doublet, t=triplet, p=pentuplet, hex=hextet, hept=heptet, m=multiplet, br.=broad, coupling constants are given in Hz); by LC-MS (Agilent MS detector G1956B with Agilent 1200 Binary Pump and DAD), $t_R$ is given in minutes.

Parameters of LC-MS Method:

| | |
|---|---|
| Injection volume: | 2 μL |
| Column: | Kinetex 2.6 micron, 2.1 × 50 mm |
| Column flow: | 1 ml/min |
| Eluents: | Eluent A: water, 0.08% TFA |
| | Eluent B: MeCN, 0.012% TFA |
| Gradient: | 2.0 min   95% B |
| | 2.8 min   95% B |
| | 3.0 min   5% B |
| Pressure | 380 bar |
| Temperature: | 40° C. |

Example 1

6-methoxy-1,5-naphthyridin-4-ol 1.i. 5-(((6-methoxypyridin-3-yl)amino)methylene)-2,
2-dimethyl-1,3-dioxane-4,6-dione A double jacketed flask was charged with 5-amino-2-methoxypyridine (500 g, 1 eq.), 2,2-dimethyl-1,3-dioxane-4,6-dione (697 g, 1.2 eq.), triethylorthoformate (740 mL, 1.1 eq.) and ethanol (4 L). The mixture was heated to reflux for one hour. The dark suspension obtained was cooled to 5° C. and the mixture was filtered. The product was washed with ethanol (1 L) and dried on a rotary evaporator to obtain a purple solid (1058 g; 95% yield).

$^1$H-NMR (CDCl$_3$): δ=11.20 (d, J=13.9 Hz, 1H), 8.51 (d, J=14.2 Hz, 1H), 8.14 (d, J=2.9 Hz, 1H), 7.54 (dd, J=8.9, 3.0 Hz, 1H), 6.85 (d, J=8.9 Hz, 1H), 3.98 (s, 3H), 1.77 (s, 6H).

LC-MS: $t_R$=1.22 min; [M+1]$^+$=279; purity: 100% a/a.

1.ii. 6-methoxy-1,5-naphthyridin-4-ol

Dowtherm A (1300 mL) was heated to 255° C. under nitrogen atmosphere with the help of an electrical heating mantle. Intermediate 1.i (161 g, 1 eq.) was dissolved in 1,3-dimethyl-imidazolidinone (500 mL) at 80° C. The solution was added to the boiling Dowtherm A over a period of about 35 min. The reaction mixture was cooled to 20° C. The mixture was filtered and slurried in ethanol (800 mL) at 80° C. The mixture was cooled to 20° C., filtered and washed with ethanol (150 mL). The product was dried on a rotary evaporator at 50° C. and below 5 mbar to yield a brown solid (69.6 g; 68% yield).

$^1$H-NMR (d6-DMSO): δ=11.78 (m, 1H), 7.97 (m, 2H), 7.17 (d, J=9.0 Hz, 1H), 6.28 (m, 1H), 3.94 (s, 3H).

LC-MS: $t_R$=0.49 min; [M+1]$^+$=177; purity: 99% a/a.

Example 2

6-methoxy-3-nitro-1,5-naphthyridin-4-ol

Fuming HNO$_3$ (500 mL) was cooled to 10-15° C. and the compound of Example 1 (80 g, 1 eq.) was added in portions over a period of 20 min. The reaction mixture was heated to 67° C. for 4 h. The mixture was cooled to 20° C. and added to ice (2 kg) with stirring. The yellow suspension was filtered and the product was washed with water (1500 mL). After drying, a yellow solid (70 g; 70% yield) was obtained.

$^1$H-NMR (d6-DMSO): δ=13.00 (m, 1H), 9.15 (s, 1H), 8.08 (d, J=9.0 Hz, 1H), 7.29 (d, J=9.0 Hz, 1H), 3.99 (s, 3H).

LC-MS: $t_R$=0.54 min; [M+1]$^+$=222; purity: 100% a/a.

Example 3

8-bromo-2-methoxy-7-nitro-1,5-naphthyridine

The compound of Example 2 (132.3 g, 1 eq.) was suspended in DMF (1200 mL) at 20° C. and PBr$_3$ (68 mL, 1.2 eq.) was added over a period of 15 min. The mixture was stirred at 65° C. for 60 min, cooled to 20° C., poured on ice (800 g) and filtered. The product was slurried in ethanol (500 mL), filtered and dried on a rotary evaporator at 65° C., affording a yellow solid (155.8 g; 92% yield).

$^1$H-NMR (d6-DMSO): δ=9.21 (s, 1H), 8.44 (d, J=9.1 Hz, 1H), 7.52 (d, J=9.1 Hz, 1H), 4.13 (s, 3H).

LC-MS: $t_R$=1.62 min; [M+1]$^+$=283; purity: 100% a/a.

Example 4

8-chloro-2-methoxy-7-nitro-1,5-naphthyridine

The compound of Example 2 (20 g, 1 eq.) was suspended in DMF (200 mL) at 20° C. To the suspension was added POCl$_3$ (27.7 g, 2 eq.) over a period of 15 min. The mixture was stirred at 25° C. for 35 min, poured on ice (200 g) and filtered. After drying on a rotary evaporator at 70° C., a yellow solid (20.5 g; 93% yield) was obtained.

$^1$H-NMR (d6-DMSO): δ=9.30 (s, 1H), 8.45 (d, J=9.1 Hz, 1H), 7.54 (d, J=9.1 Hz, 1H), 4.12 (s, 3H).

LC-MS: $t_R$=1.52 min; [M+1]$^+$=240; purity: 100% a/a.

Example 5

6-methoxy-1,5-naphthyridin-3-amine

Variant 1:

The compound of Example 3 (60 g, 1 eq.) was suspended in methanol (600 mL) in a 1 L Parr autoclave equipped with gas stirrer and thermometer. To the suspension was added Raney nickel (about 20 g). The autoclave was inertized before being set under hydrogen (5 bar) and the mixture was stirred for 2 h. To the reaction mixture was added stepwise TEA (59 ml, 2 eq) and Raney nickel (about 10 g). The mixture was hydrogenated at 10 bar and 50° C. for 3 h. To the reaction mixture was added activated charcoal (7 g). The reaction mixture was heated to 60° C. (ET) and filtered over Celite (70 g) at elevated temperature. The nutsche was rinsed with methanol (280 mL) at 20° C. To the combined filtrates was added water (120 mL). The yellow solution was concentrated on a rotary evaporator at 60° C. and under reduced pressure. 800 mL solvent were removed, resulting in a thick suspension. The suspension was cooled to 5° C. and filtered. The product was washed with water (50 mL). The product was dried on a rotary evaporator at 75° C. and under a pressure below 20 mbar. An off-white, slightly yellow solid (28.4 g; 77% yield) was obtained.

$^1$H-NMR (d6-DMSO): δ=8.28 (d, J=2.5 Hz, 1H), 7.97 (d, J=8.9 Hz, 1H), 7.04 (d, J=2.5 Hz, 1H), 6.79 (d, J=8.9 Hz, 1H), 5.92 (s, 2H), 3.94 (s, 3H).

LC-MS: $t_R$=0.71 min; [M+1]$^+$=176; purity: 100% a/a.

Variant 2:

The compound of Example 4 (30 g, 1 eq.) was suspended in methanol (300 mL) in a 1 L Parr autoclave equipped with gas stirrer and thermometer. To the suspension was added Raney nickel (about 18 g). The autoclave was inertized before being set under hydrogen (5 bar) and the mixture was stirred for 2.5 h. To the reaction mixture was added 5.4M NaOMe in MeOH (47 ml, 2 eq). To the mixture was added water wet Raney nickel (about 3 g). The mixture was hydrogenated at 10 bar and 50° C. for 12 h. The reaction mixture was filtered over Celite at 20° C. The nutsche was rinsed with methanol (300 mL) at 20° C. The combined filtrates were concentrated on a rotary evaporator at 60° C. and under reduced pressure to yield a yellow solid (13.5 g; 62% yield).

LC-MS: purity: 100% a/a.

Example 6

7-fluoro-2-methoxy-1,5-naphthyridine

Variant 1:

In a 0.5 L flask was added the compound of Example 5 (27 g, 1.0 eq.) and THF (200 mL). The suspension was cooled to −20° C. and BF₃ etherate (49 ml, 2.5 eq.) was added dropwise, yielding a yellow solution. At −20° C., tert-butyl nitrite (22.3 ml, 1.1 eq.) was added. A yellow suspension was formed. The reaction was allowed to warm to 25° C. The yellow suspension was stirred at 25° C. for 15 min. The yellow suspension was filtered and the diazonium salt was washed with Hept (3×25 mL). The diazonium salt was dried on a rotary evaporator at 20° C. and under 5 mbar pressure for a few minutes. Hept (200 mL) was heated to 85° C. and the diazonium salt (41 g) was added thereto in 10 portions over a period of 30 min. A thick oil was formed. After the addition was completed, the mixture was stirred for 10 min at 85° C. The mixture was cooled to 20° C. EA (250 mL) and water (250 mL) were added. The mixture was stirred for 5 min. The layers were separated and the org. layer was washed with water (200 mL). The org. layer was filtered over Na₂SO₄ (20 g) to remove some precipitates. The filtrate was concentrated to dryness on a rotary evaporator at 55° C. and under a pressure below 20 mbar. A yellow crystalline solid (22.3 g; 81% yield) was obtained.

¹H-NMR (d6-DMSO): δ=8.86 (d, J=2.7 Hz, 1H), 8.32 (d, J=9.0 Hz, 1H), 8.07 (dd, J=10.0, 2.4 Hz, 1H), 7.26 (d, J=9.1 Hz, 1H), 4.03 (s, 3H).

LC-MS: $t_R$=1.22 min; [M+1]⁺=176; purity: 100% a/a.

Variant 2:

A 200 mL perfluoralkoxyalkane flask was charged with liquid HF (60 g, 105 eq.) at −40° C. and Pyr (26.1 g, 11.56 eq). Sodium nitrite (2.2 g, 1.1 eq.) was added at −50° C. The compound of Example 5 (5 g, 1.0 eq.) was added to the reaction mixture over a period of 10 min at −50 to −40° C. The yellow solution was warmed to 20° C. and then to 65° C. The mixture was stirred at 60° C. for 2 h. The mixture was cooled to 0° C. and poured to ice (100 g) and EA (80 mL). 25% aq. ammonia (90 mL) was added. The aq. layer was extracted twice with EA (2×20 mL). The org. layers were washed with water (20 mL). The combined org. layers were dried and evaporated in vacuo at 50° C. to dryness. A yellow crystalline solid (4.80 g; 90% yield) was obtained.

LC-MS: purity: 94.4% a/a.

Variant 3:

A 200 mL perfluoralkoxyalkane flask was charged with liquid HF (60 g, 105 eq.) at −40° C. and Pyr (26.1 g, 11.56 eq). The compound of Example 5 (5 g, 1.0 eq.) was added thereto over a period of 10 min at −50 to −40° C. The solution was warmed to −5° C. and sodium nitrite (2.2 g, 1.1 eq.) was added at −9 to −5° C. The reaction mixture was warmed to 10° C. and stirred for one hour. The mixture was cooled to −30° C. and transferred to a Monel stirring autoclave and heated to 65° C. within 30 min. During the heating-up a pressure increase to 6.6 bar occurred, indicating the liberation of nitrogen gas. Upon evaporation of the HF, the residue was poured into ice/EA and 25% aq. ammonia (40 mL). The aq. phase was extracted twice with EA (2×20 mL) and the org. phases were washed with water (20 mL). The org. phases were dried and evaporated to dryness.

A yellow crystalline solid (4.84 g; 90% yield) was obtained.

LC-MS: purity: 99.3% a/a.

The invention claimed is:

1. A method for manufacturing a compound of formula (I-5)

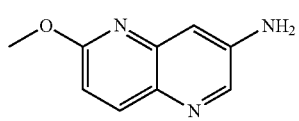

or a salt thereof, comprising reacting a compound of formula (I-2)

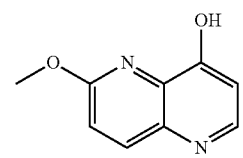

with a nitration reagent or mixture of reagents at a temperature from 20° C. to 100° C.

2. A method for manufacturing a compound of formula (I-5)

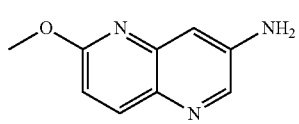

comprising reacting the compound of formula (I-4)

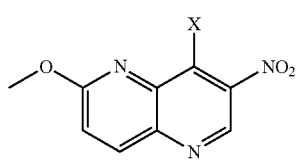

wherein X is Br or Cl, with hydrogen in an alkanol in the presence of a base and of a catalyst selected from Raney nickel, iron, palladium or platinum.

3. The method of claim 2, wherein the base is triethylamine.

4. The method of claim 2, wherein the alkanol is methanol.

5. The method of claim 2, wherein the catalyst is Raney nickel.

6. The method of claim 1, wherein the reaction of the compound of formula (I-2) with the nitration reagent or mixture of reagents is performed at a temperature from 50° C. to 70° C.

7. The method of claim 1, wherein the compound of formula (I-2) is reacted with nitric acid having a concentration of at least 65% in weight.

8. The method of claim 1, further comprising a) obtaining a compound of formula (I-3)

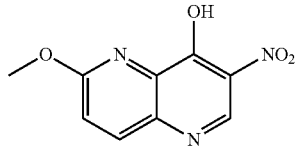

I-3 by reacting the compound of formula (I-2) with a nitration reagent or mixture of reagents at a temperature from 20° C. to 100° C.;

b) reacting the compound of formula (I-3) obtained after step a) with pentachlorophosphorane, tribromophosphine, trichlorophosphine, phosphoryl tribromide or phosphoryl trichloride to obtain a compound of formula (I-4)

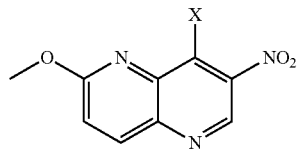

I-4 wherein X is Br or Cl;

c) reacting the compound of formula (I-4) obtained after step b) with hydrogen in an alkanol in the presence of a base and a catalyst selected from Raney nickel, iron, palladium or platinum to obtain the compound of formula (I-5).

* * * * *